(12) United States Patent
Arnin et al.

(10) Patent No.: US 7,736,369 B2
(45) Date of Patent: Jun. 15, 2010

(54) INSERTING ANTERIOR AND POSTERIOR SPINAL PROSTHESES

(75) Inventors: Uri Arnin, Kiryat Tivon (IL); Shai Fleischer, Haifa (IL)

(73) Assignee: Impliant Ltd., Ramat Poleg, Netanya (IL)

( * ) Notice: Subject to any disclaimer, the term of this patent is extended or adjusted under 35 U.S.C. 154(b) by 922 days.

(21) Appl. No.: 11/401,305

(22) Filed: Apr. 11, 2006

(65) Prior Publication Data

US 2006/0241642 A1 Oct. 26, 2006

Related U.S. Application Data

(60) Provisional application No. 60/669,902, filed on Apr. 11, 2005, provisional application No. 60/757,467, filed on Jan. 10, 2006.

(51) Int. Cl.
*A61F 5/00* (2006.01)

(52) U.S. Cl. .............. 606/86 A; 606/86 R; 606/99; 623/17.16

(58) Field of Classification Search .............. 606/86 R, 606/87–89, 96–99, 246–249, 53–54, 86 A, 606/102, 105, 914, 916; 623/17.11–17.16
See application file for complete search history.

(56) References Cited

U.S. PATENT DOCUMENTS

| | | | | |
|---|---|---|---|---|
| 5,431,658 A | * | 7/1995 | Moskovich | 606/99 |
| 5,782,830 A | * | 7/1998 | Farris | 606/99 |
| 5,928,139 A | * | 7/1999 | Koros et al. | 600/205 |
| 6,428,544 B1 | * | 8/2002 | Ralph et al. | 606/99 |
| 6,478,800 B1 | * | 11/2002 | Fraser et al. | 606/99 |
| 6,485,518 B1 | * | 11/2002 | Cornwall et al. | 623/17.11 |
| 6,530,929 B1 | * | 3/2003 | Justis et al. | 606/103 |
| 6,599,294 B2 | * | 7/2003 | Fuss et al. | 606/99 |
| 6,652,533 B2 | * | 11/2003 | O'Neil | 606/100 |
| 6,652,534 B2 | * | 11/2003 | Zucherman et al. | 606/102 |
| 6,712,825 B2 | * | 3/2004 | Aebi et al. | 606/90 |
| 2003/0171750 A1 | * | 9/2003 | Chin | 606/61 |
| 2004/0030346 A1 | * | 2/2004 | Frey et al. | 606/99 |
| 2004/0176779 A1 | * | 9/2004 | Casutt et al. | 606/102 |
| 2004/0177494 A1 | * | 9/2004 | Link et al. | 29/743 |
| 2004/0220567 A1 | * | 11/2004 | Eisermann et al. | 606/61 |
| 2005/0256578 A1 | * | 11/2005 | Blatt et al. | 623/17.15 |

FOREIGN PATENT DOCUMENTS

WO 01/41681 6/2001

* cited by examiner

*Primary Examiner*—Thomas C Barrett
*Assistant Examiner*—Larry E Waggle, Jr.
(74) *Attorney, Agent, or Firm*—Dekel Patent Ltd.; David Klein (57) ABSTRACT

Spinal apparatus is disclosed that includes reference structure spatially fixed relative to a plurality of pedicle screws that are mounted in adjacent vertebrae of a patient, and a device connected to the reference structure which is adapted to install an anterior spinal prosthesis, wherein the reference structure defines a spatial relationship between the anterior spinal prosthesis and a posterior spinal prosthesis attached to the pedicle screws.

5 Claims, 9 Drawing Sheets

FIG. 6 ic # INSERTING ANTERIOR AND POSTERIOR SPINAL PROSTHESES

CROSS-REFERENCE TO RELATED APPLICATIONS

This application claims priority under 35 USC §119 to U.S. Provisional Patent Application Ser. No. 60/669,902, filed Apr. 11, 2005, and U.S. Provisional Patent Application Ser. No. 60/757,467, filed Jan. 10, 2006, which are incorporated herein by reference.

FIELD OF THE INVENTION

The present invention relates to human prostheses, and more particularly to spinal column vertebral disc prosthesis in conjunction with posterior spinal prostheses and methods for the insertion and harmonious coordination between the prostheses.

BACKGROUND OF THE INVENTION

A common procedure used for stabilizing the vertebral column is bracing adjacent vertebrae by connecting rigid or resilient connecting implants to anchor members such as pedicle screws. Rigid stabilization (fusion) of the spinal column can be disadvantageous due to migration of the problems to adjacent level in the spinal column. Dynamic stabilization provided by resilient implant on the other hand offer a possibility of reduced damage to the adjacent level. This is because it allows for motion preservation, near normal distribution of stress along the spine.

A common approach is an anterior approach which involves going through a patient's abdomen. This is a complex procedure often involving extensive vessel retraction among other difficulties. A posterior approach can alleviate some of these problems. The placement of implants in the disc space from a posterior lateral approach has been described that allows unilateral or bilateral disc space preparation and implant insertion to provide stability to the subject disc space.

However when a disc prosthesis is to be inserted either in conjunction with or subsequent to a procedure involving a spinal posterior prosthesis, involving the use of pedicular screws, there is a need to take into account the relative positioning of the disc prosthesis in relation to the posterior prosthesis in particular when at least one of them involves articulation and also in relationship to the vertebrae and disc morphology.

SUMMARY OF THE INVENTION

The present invention seeks to provide a spinal column vertebral disc prosthesis in conjunction with posterior spinal prostheses and methods for the insertion and harmonious coordination between the prostheses, as described more in detail hereinbelow.

According to some embodiments of the present invention, a plurality (such as, but not limited to, at least three) of pedicle screws are placed in position in preferably adjacent vertebra of a patient who is a suitable candidate for receiving a posterior implant and a disc prosthesis. The methods of introducing pedicular screws are known in the art. Once the pedicle screws are in place, the vertebral disc insertion device is connected to the pedicle screws that are inserted in two vertebrae. Following the connection of the disc insertion device to the pedicle screws, distractors may be used to distract the two vertebrae by means that are also known to those skilled in the art.

The device may define a trajectory or path or reference point, for the insertion of the disc prosthesis. This trajectory or path or reference point ensures that the implanted disc will be placed in a predetermined position in relation to the pre-inserted screws. Since the screws are in a known position in relation to the vertebra and to a posterior implant to be subsequently placed onto the pedicle screws, this device will aid in the placement of the disc prosthesis preferably via a transforaminal approach (such a disc insertion approach being known in the art) in an accurate position in relation to both the vertebrae and to the posterior implant, thus minimizing human error. The positioning of the pedicle screws defines the positioning of the posterior prosthesis.

The device according to embodiments of this invention combines the functions of attachment to pedicle screws, distraction of two vertebrae and the insertion of a disc prosthesis using a predetermined trajectory or reference point.

There is thus provided in accordance with an embodiment of the present invention a method for inserting spinal prostheses including providing reference structure spatially fixed relative to a plurality of pedicle screws that are mounted in adjacent vertebrae of a patient, installing an anterior spinal prosthesis with a device that is connected to the reference structure, and installing a posterior spinal prosthesis to the pedicle screws, wherein the reference structure defines a spatial relationship between the anterior and posterior spinal prostheses. The adjacent vertebrae may be distracted before installing the anterior spinal prosthesis. The reference structure defines a path for insertion of the anterior spinal prosthesis in relation to the pedicle screws.

There is also provided in accordance with an embodiment of the present invention a spinal apparatus including reference structure spatially fixed relative to a plurality of pedicle screws that are mounted in adjacent vertebrae of a patient, and a device connected to the reference structure which is adapted to install an anterior spinal prosthesis, wherein the reference structure defines a spatial relationship between the anterior spinal prosthesis and a posterior spinal prosthesis attached to the pedicle screws.

The spinal apparatus may further include a positioning adapter attachable to a plurality of (e.g., at least three) pedicle screws, the positioning adapter including a pair of connecting devices, each connecting device including a pair of arms that extend outwards corresponding to a spacing of a pair of pedicle screws mounted on a particular vertebra, the arms being attachable to that pair of pedicle screws, wherein the connecting devices are formed with the reference structure, wherein the device includes a disc implant holder adapted to hold an anterior spinal prosthesis, and further including a connecting element adapted to fix the disc implant holder to the positioning adapter with respect to the reference structure.

The positioning adapter may be attached to a distraction device adapted to distract two vertebrae to which the pedicle screws are attached.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF EMBODIMENTS

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
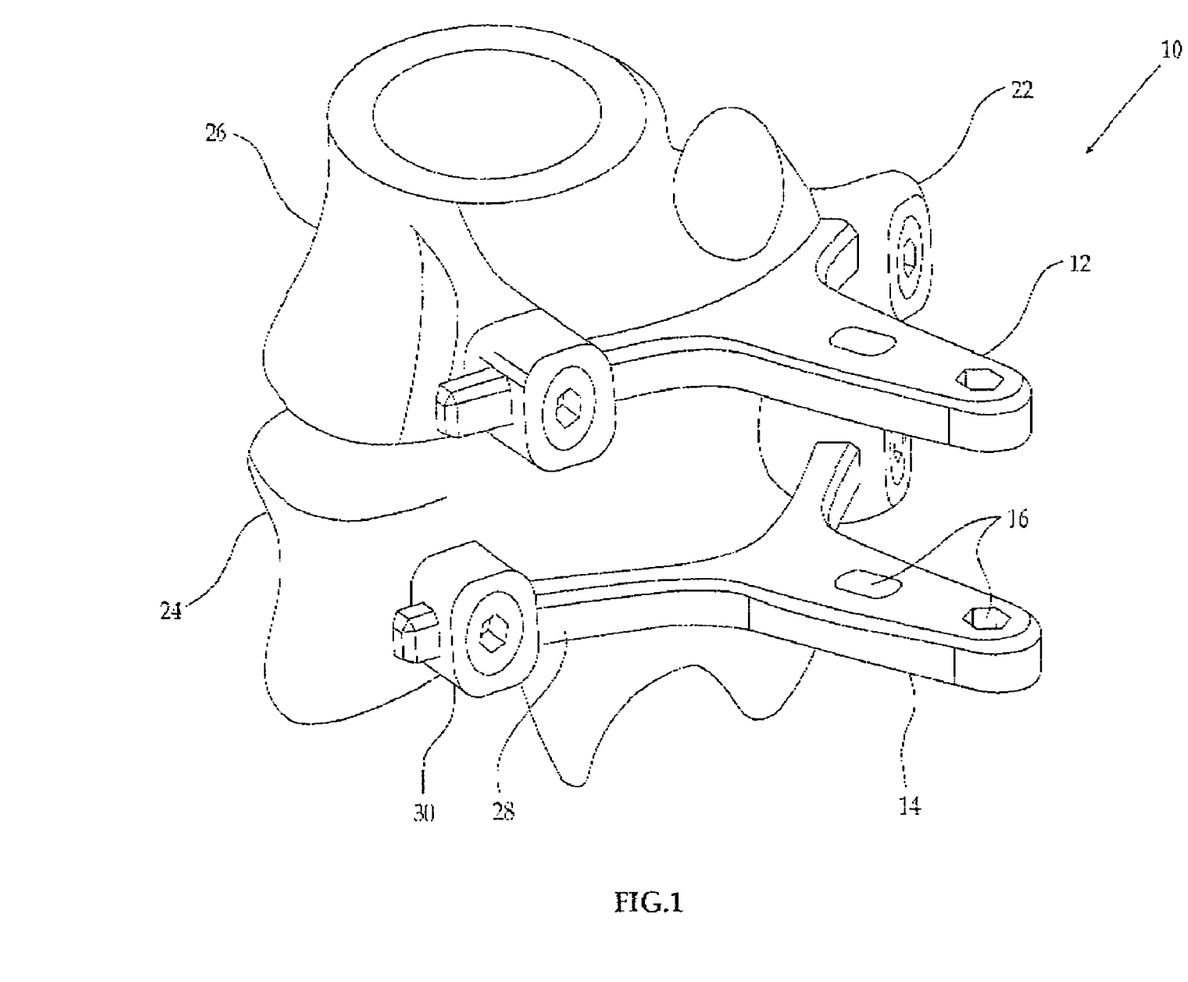
FIG. 1 is an isometric view of two vertebrae with pedicle screws in place and positioning adapter fixed to the pedicle screws.

Reference is now made to FIG. 1, which illustrates a positioning adapter 10 attached to four pedicle screws 22 which are anchored into two adjacent vertebrae, for example, L4 24 and L5 26. The screws 22 were initially placed into the pedicle of the vertebrae as is known to those skilled in the art. The pedicle screws 22 may be used, for example, to anchor a posterior spinal prosthesis to the pedicles.

Although four pedicle screws are shown here in this non-limiting example of the application of positioning adapter 10, a minimum of three anchoring elements such as pedicle screws are sufficient for the successful implementation of positioning adapter 10. The attachment points from two vertebrae define a plane and connect two adjacent vertebrae.

Positioning adapter 10 may include a pair of connecting devices 12 and 14. Each connecting device may be shaped as a planar flange with a pair of arms 28 that extend outwards corresponding to the spacing of the pedicle screws 22. Arms 28 are preferably sufficiently long to accommodate most any spacing of the screws 22. Alternatively, a set of positioning adapters 10 may be provided to span any range of spacing of the screws 22. The arms 28 of positioning adapter 10 may be attached to the vertebrae by inserting the arms into the heads 30 of screws 22. As the screws are positioned in their correct place, so positioning adapter 10 is now positioned in place for the next stage of the procedure which is the distraction of the two vertebrae.

Each vertebra has its own connecting device as illustrated in FIG. 1. The connecting devices 12 and 14 may be formed with reference structure 16, such as but not limited to, points, pivots or apertures, for example, holes. In summary, positioning adapter 10 is configured to be connected to pedicle screws 22 and has reference structure 16 (also referred to as reference positioning points 16) for proper placement and registration of an anterior disc prosthesis with respect to a posterior spine prosthesis, as is described hereinbelow.

Figure 2:
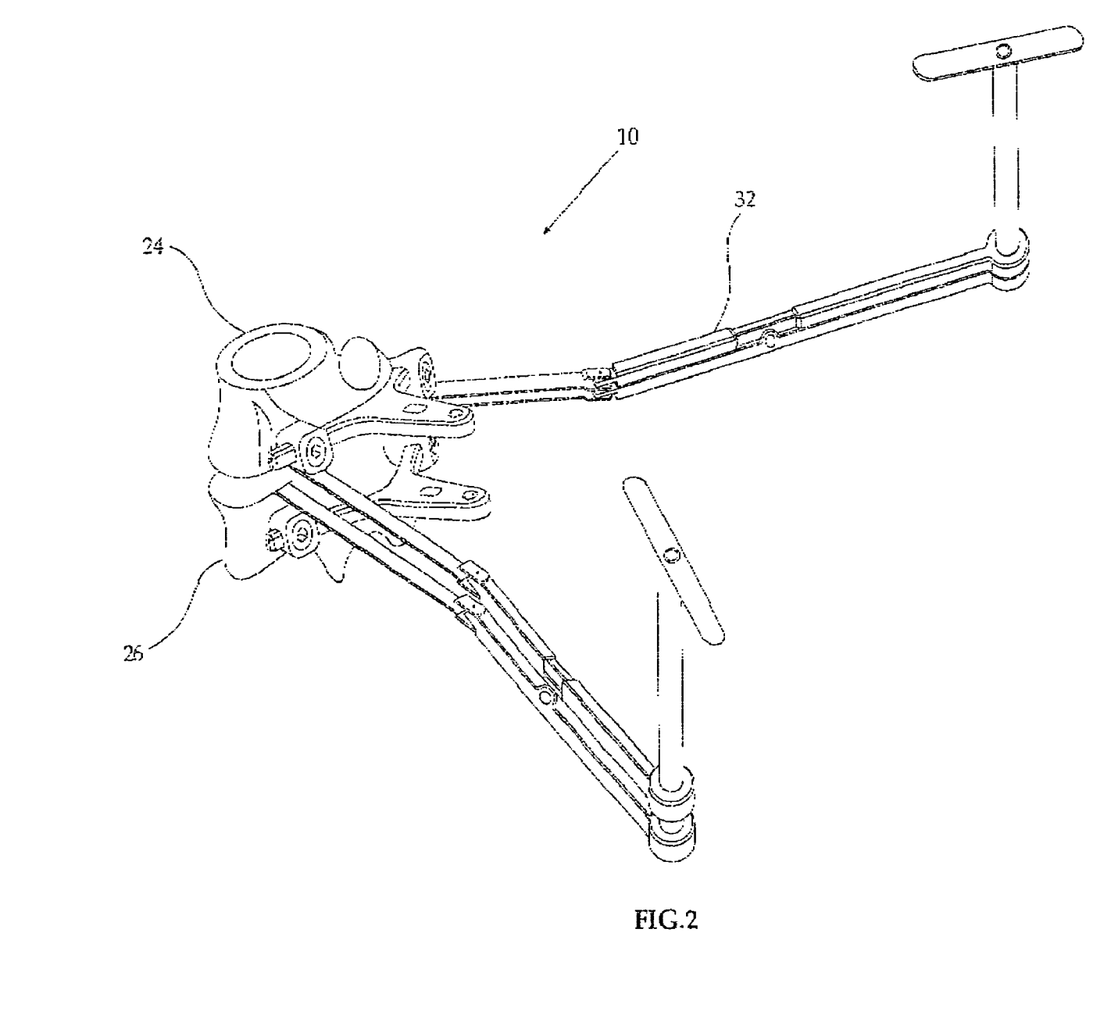
FIG. 2 is an isometric view of the positioning adapter and two distraction devices.

Reference is now made to FIG. 2, which is a side view of a distraction device 32 in place attached to screws 22. Distraction devices are known in the art and are commercially available, such as the Distraction Forceps with hinged handle for pedicle screws, manufactured by Synthes Spine, 1302 Wrights Line East, West Chester, Pa. 19380. The purpose of distraction is to temporarily expose the posterior disc space in order to ease discectomy and the delivery of the disc implant. FIG. 2 illustrates distraction device 32 assembled on the pedicle screws 22. It is noted that positioning adapter 10 does not interfere with the positioning or functionality of distraction device 32.

Figure 3A:
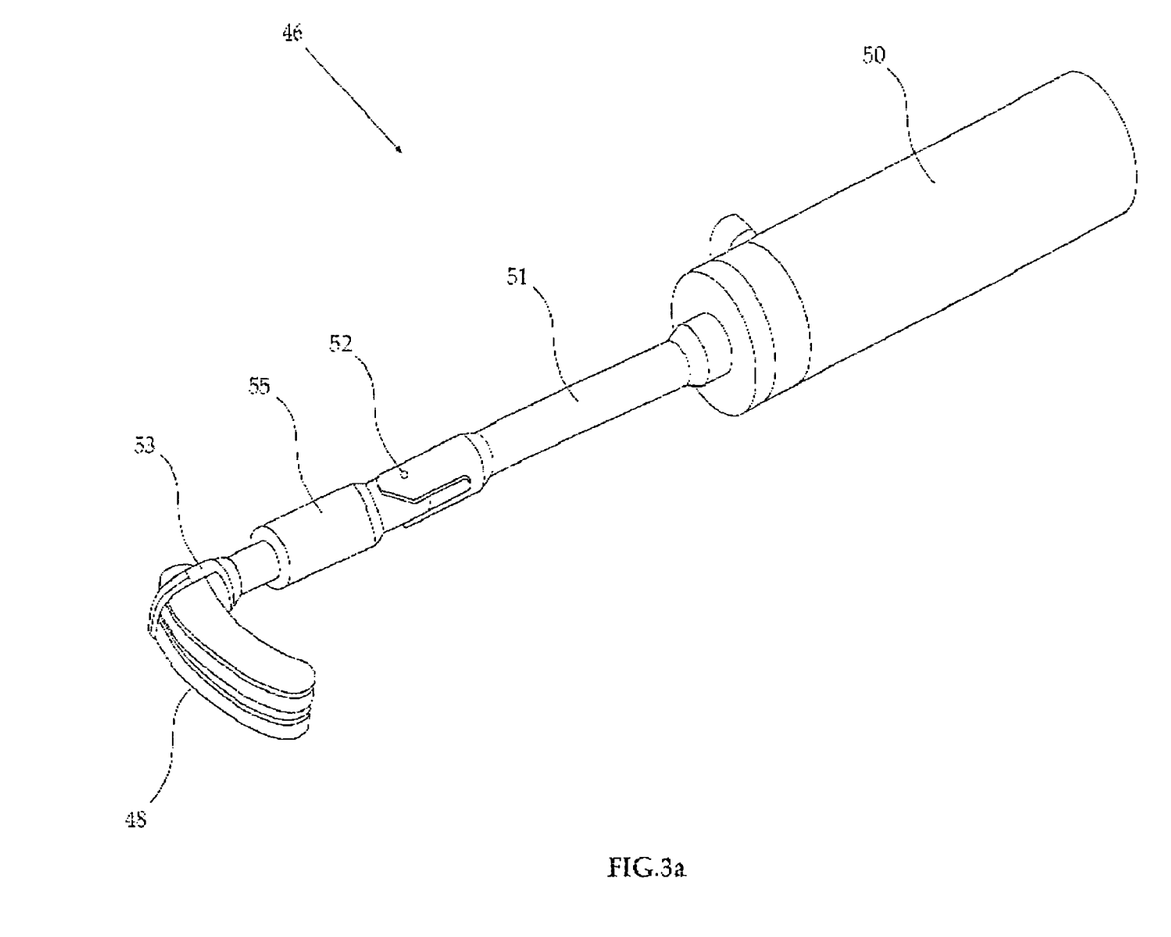
FIGS. 3A-D are isometric and top views of a disc implant holder.
Figure 3B:
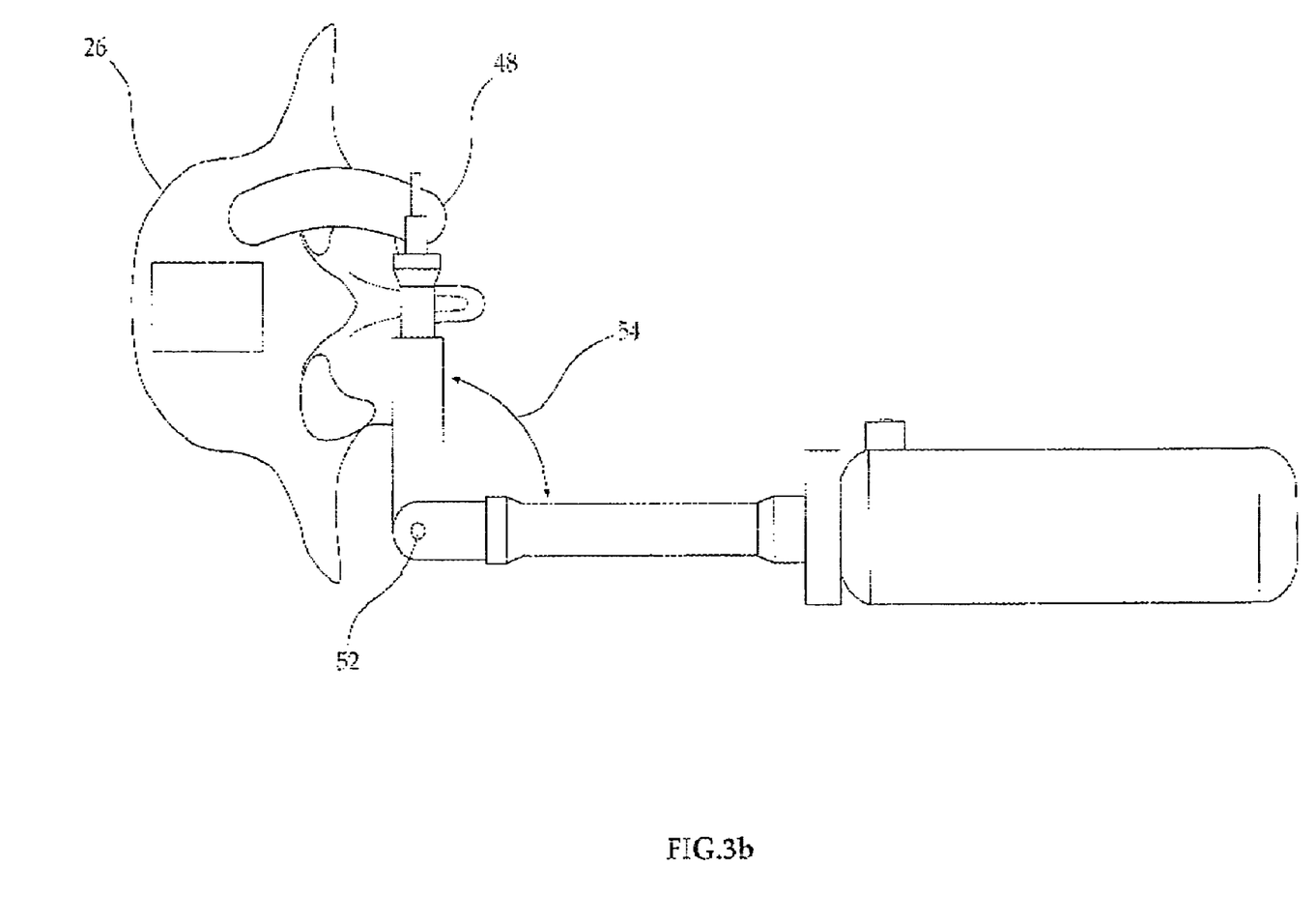

Following discectomy and endplate preparation, the next function of positioning adapter 10 can be implemented. Reference is now made to FIGS. 3A-3B, which illustrate a disc implant holder 46 which is used for inserting an artificial disc into the intervertebral disc space, while providing the surgeon with freedom of movement in the workspace of the spinal operation. The disc implant holder 46 may include a handle 50 from which extends a proximal shaft 51. A distal shaft 55 may be pivotally attached to proximal shaft 51 at a pivot 52. The pivot 52 may be, for example, a pinned connection that allows free movement of the proximal shaft 51 relative to distal shaft 55. Alternatively, pivot 52 may be, for example, a ratcheted connection that allows ratcheted movement of the proximal shaft 51 relative to distal shaft 55. More than one pivoted connection may be provided to allow other degrees of movement of the shafts. The distal shaft 55 may include a pair of clamping jaws 53. Jaws 53 may be spring-baised to be normally closed and may be opened by pressing or squeezing them to spread them apart, or by means of some opening handle or cam, as is well known in the art of clamps, pliers and the like. Jaws 53 may clamp tightly on an artificial disc prosthesis or implant 48 (also referred to as anterior prosthesis 48).

The anterior prosthesis 48 may be, without limitation, an articulating prosthesis. A suitable articulating anterior prosthesis is described in U.S. patent application Ser. No. 10/898,229 (corresponding to PCT Application WO 2005/084590) to Arnin, et al., the disclosure of which is incorporated herein by reference. PCT Application WO 2005/084590 describes an endoprosthesis including a first articulating member formed with a generally concave articulating surface, and a second articulating member formed with a generally convex articulating surface which articulates with the concave articulating surface, the first and second articulating members each having a generally planar attachment surface for attachment to spine structure.

Figure 3C:
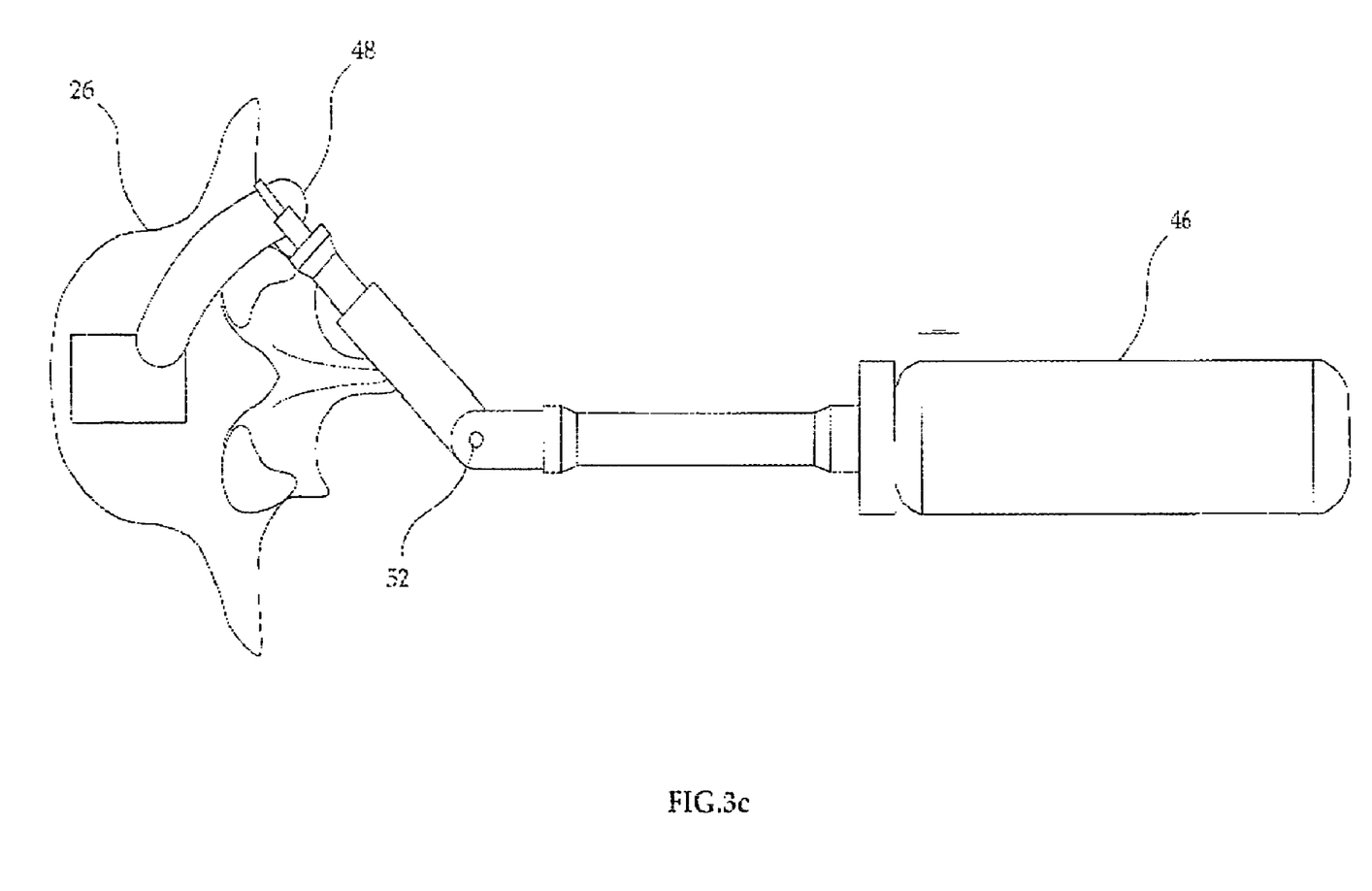
Figure 3D:
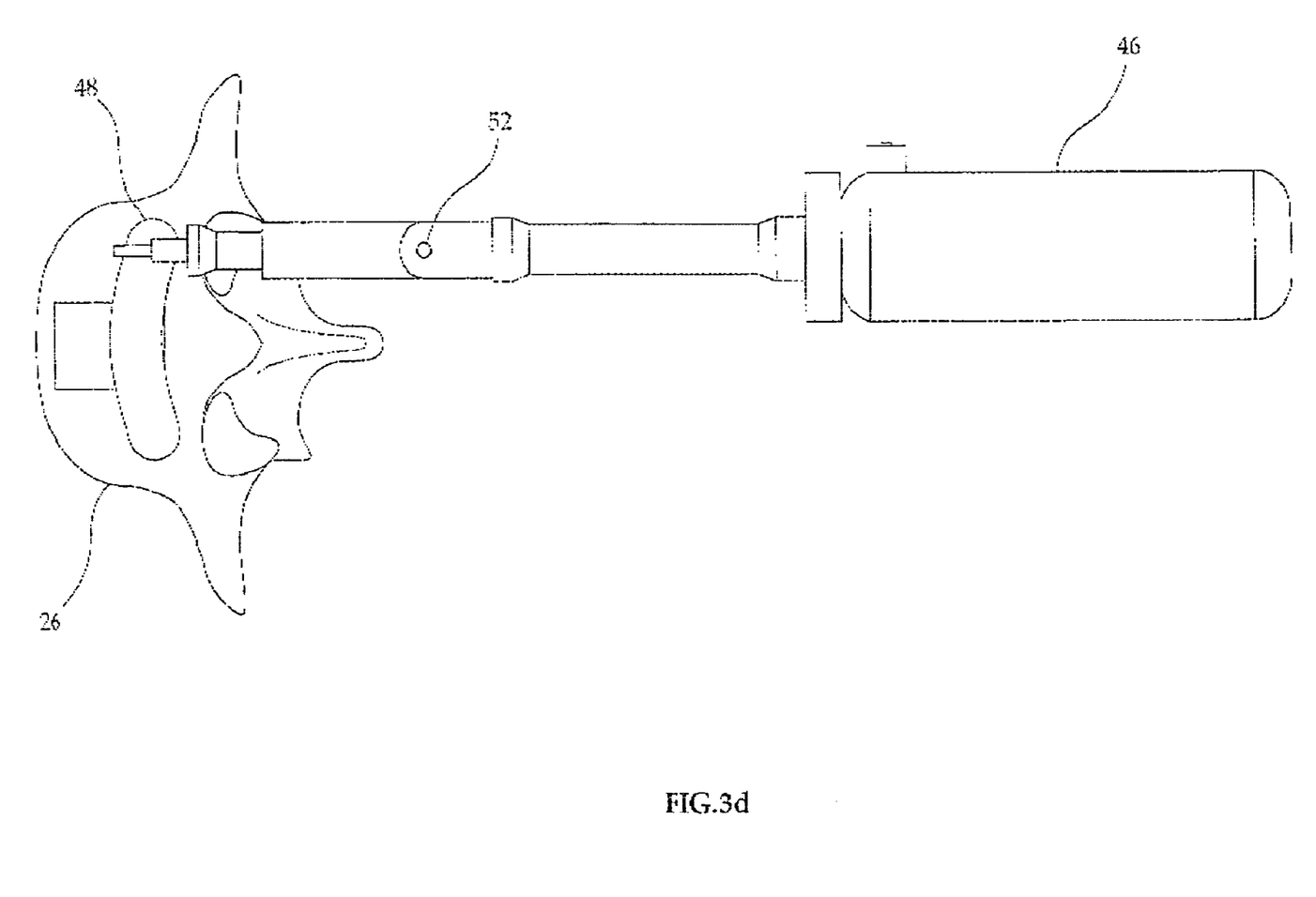

Reference is now made to FIGS. 3B-3D, which illustrate the disc implant holder 46 in the spinal procedure workspace. The spinal disc prosthesis or implant 48 may be attached to one end of disc implant holder 46 and handle 50 may be used for placing, guiding and pushing the implant 48 into workspace. FIG. 3B illustrates the first step of the insertion of the artificial disc into the intervertebral disc space using for example a TLIF (Transforaminal Lumbar Interbody Fusion) procedure known in the art. Pivot 52 provides the surgeon the ability to swing proximal shaft about an angle 54 relative to distal shaft 55 to facilitate the initial placement of the implant 48. Handle 46 may be used by the surgeon to vary the angle 54 about pivot 52 (FIGS. 3B, 3C and 3D).

Figure 4:
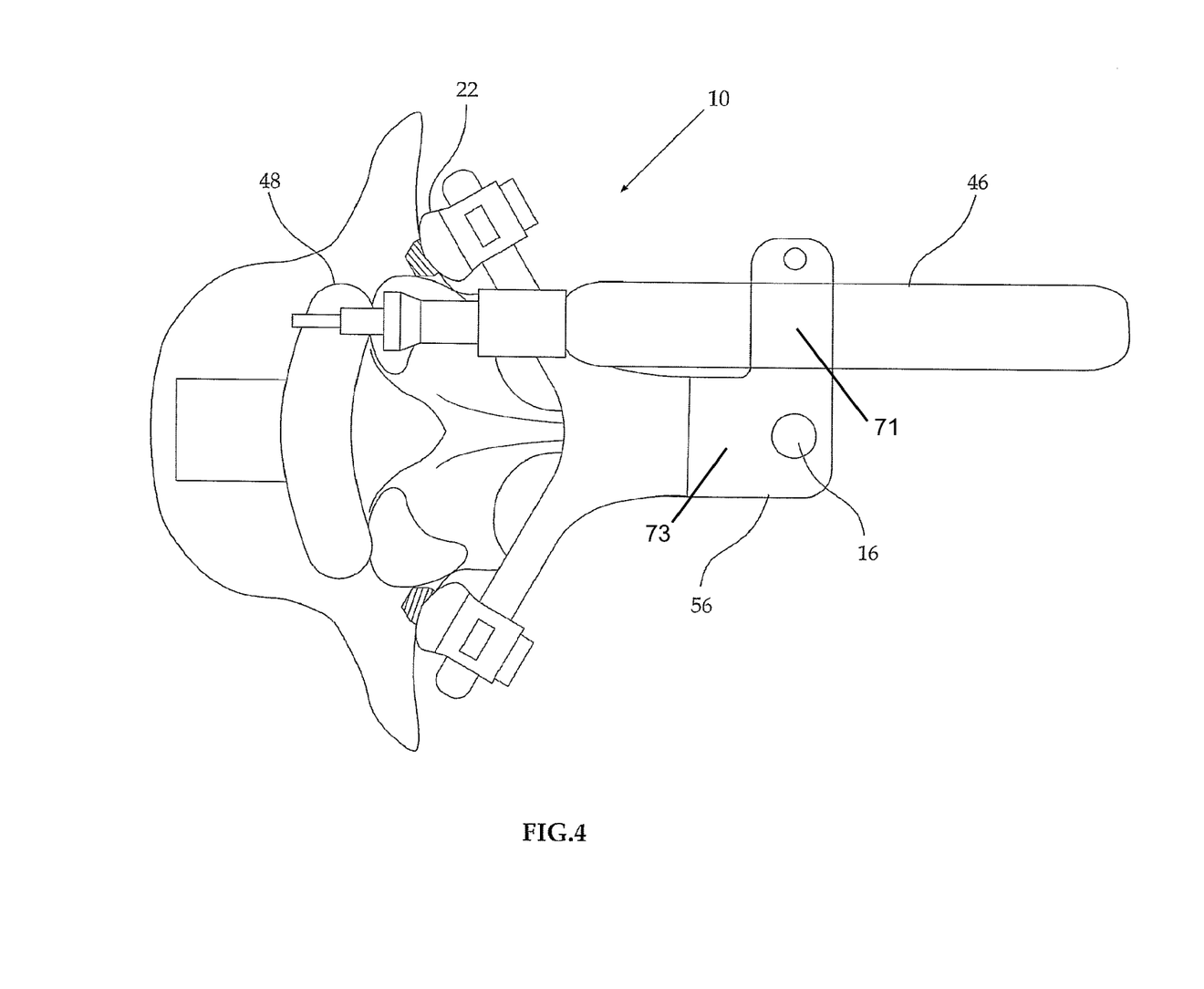
FIG. 4 is a top view of a vertebra with the disc implant holder connected to the positioning adapter.

Reference is now made to FIG. 4. After initial placement of the implant 48, positioning adapter 10 may be connected to disc implant holder 46 with a connecting element 56 (FIG. 4). Connecting element 56 fixes disc implant holder 46 to positioning adapter 10. For example, without limitation, connecting element 56 may include a tubular portion 71 through which the proximal shaft of disc implant holder 46 passes and a flange portion 73 that is fixedly attached to positioning adapter 10 at the reference positioning points 16 (FIG. 1), such as by means of mechanical fasteners (e.g., pins, screws). Connecting element 56 defines the final positioning of implant 48 in relation to the pedicle screws 22. Reference positioning points 16 define the ideal relative positioning between implant 48 and screws 22. A correct positioning of implant 48 in relation to screws 22 will provide a merging of the centers of rotation of implant 48 and spinal posterior implant that is to be attached to screws 22. It may also provide a correct load sharing between the anterior and posterior inserts. This will facilitate a close to natural range of motion and load sharing of the functional spinal unit.

Figure 5:
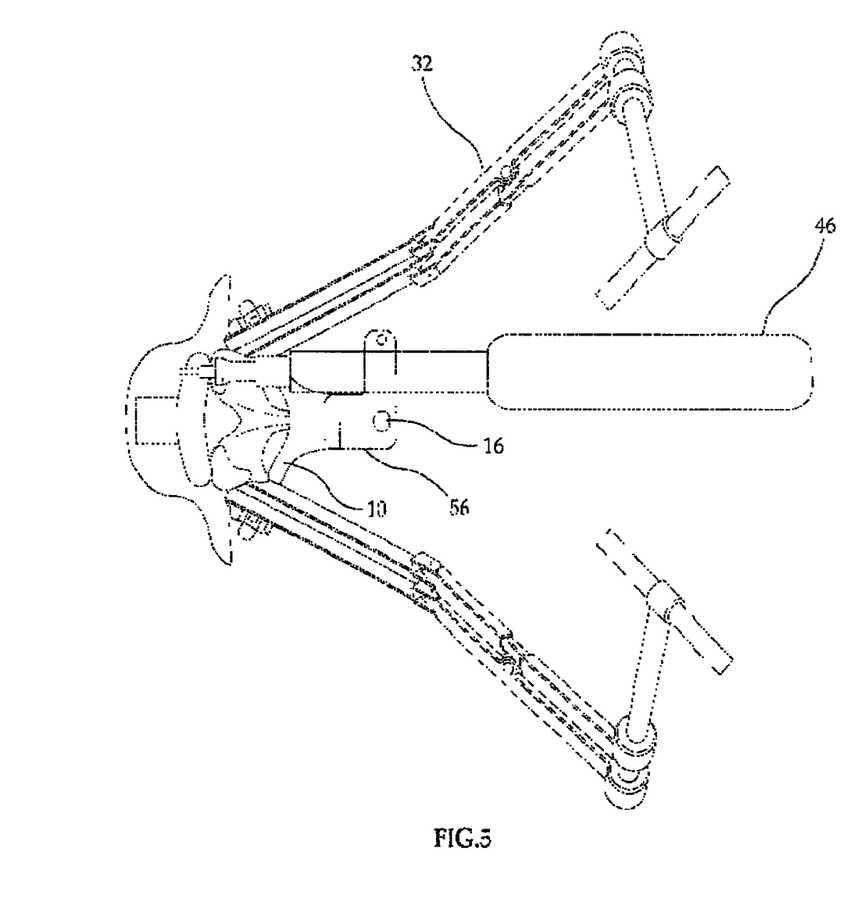
FIG. 5 is a top view of a vertebra with the disc implant holder connected to the positioning adapter and the distraction device in place.

FIG. 5 illustrates the workspace of the operation once again with only L5 visible from a top view for a clarified depiction of the devices. Distraction device 32, positioning adapter 10, and disc implant holder 46 are seen together with positioning adapter 10 and disc implant holder 46 being connected at connecting point 56.

Figure 6:
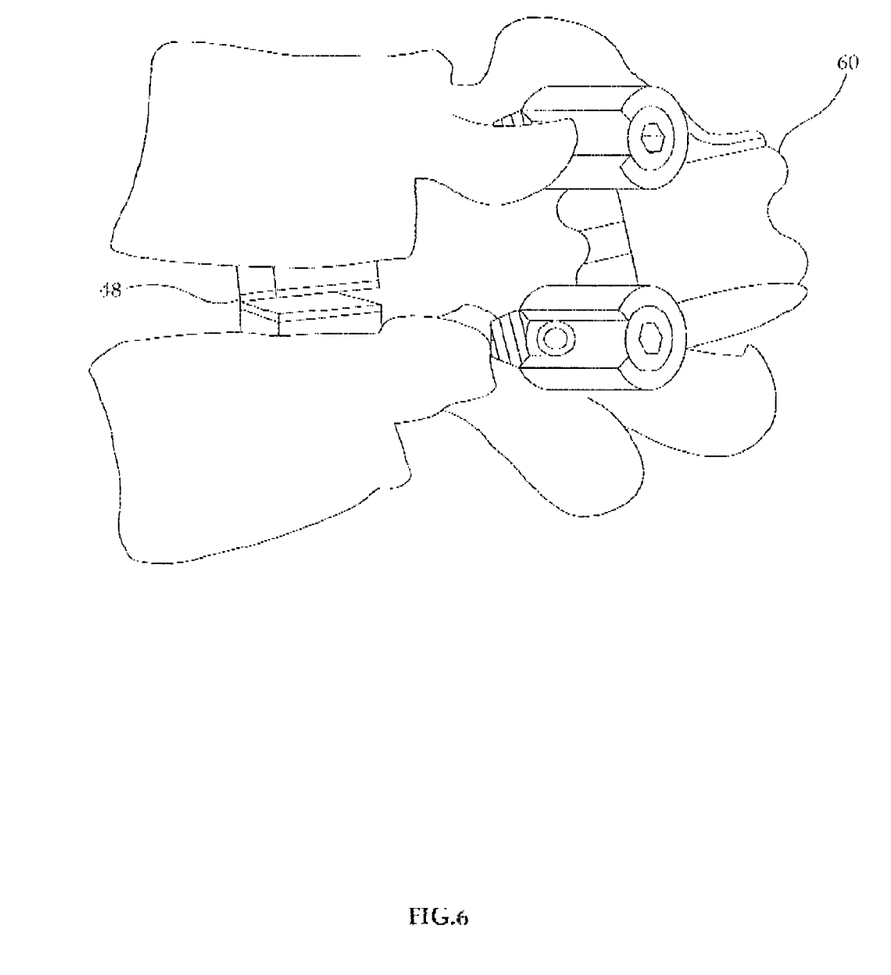
FIG. 6 is a side view of two vertebrae with an anterior disc prosthesis and a posterior prosthesis in place.

Reference is now made to FIG. 6. After installation of anterior prosthesis 48, a posterior prosthesis 60 may be attached to the pedicle screws 22. FIG. 6 illustrates two adjacent vertebrae with an anterior prosthesis 48 and posterior prosthesis 60 each in their respective correct position in relation to each other according to the embodiments of the present invention. In essence, according to the embodiments of this invention, an artificial disc, will work more efficiently if it articulates around same center of rotation with a posterior implant (e.g., facet replacement).

A suitable posterior prosthesis is described in U.S. Pat. No. 7,011,685 to Arnin, et al., the disclosure of which is incorporated herein by reference. U.S. Pat. No. 7,011,685 describes a spinal prosthesis having a unitary body with at least three attachment points attachable to spinal structure, the unitary body including a flexure assembly positioned between first and second attachment members, wherein flexure of the flexure assembly permits movement of the first attachment member relative to the second attachment member.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. Spinal apparatus comprising:
a reference structure spatially fixed relative to a plurality of pedicle screws that are adapted to be mounted in adjacent vertebrae of a patient;
a device connected to said reference structure which is adapted to install an anterior spinal prosthesis, wherein said reference structure defines a spatial relationship between said anterior spinal prosthesis and a posterior spinal prosthesis attached to said pedicle screws; and
a positioning adapter attached to a plurality of pedicle screws, said positioning adapter comprising a pair of connecting devices, each connecting device comprising a pair of arms that extend outwards corresponding to a spacing of a pair of pedicle screws mounted on a particular vertebra, said arms being attached to that pair of pedicle screws, wherein said connecting devices are formed with said reference structure;
wherein said device comprises a disc implant holder adapted to hold an anterior spinal prosthesis, and further comprising a connecting element adapted to fix said disc implant holder to said positioning adapter with respect to said reference structure.

2. The spinal apparatus according to claim 1, wherein said positioning adapter is attached to a distraction device adapted to distract two vertebrae to which the pedicle screws are attached.

3. The spinal apparatus according to claim 1, wherein said disc implant holder comprises a handle from which extends a proximal shaft, and a distal shaft pivotally attached to said proximal shaft at a pivot, wherein said distal shaft comprises a pair of clamping jaws adapted to hold the anterior spinal prosthesis.

4. The spinal apparatus according to claim 1, wherein said connecting element comprises a tubular portion through which a portion of said disc implant holder passes and a flange portion that is fixedly attachable to said positioning adapter at said reference structure.

5. The spinal apparatus according to claim 4, wherein a portion of said disc implant holder passes through said tubular portion anteriorly towards said anterior spinal prosthesis and another portion of said disc implant holder extends posteriorly through said tubular portion.

* * * * *